United States Patent [19]

Watlington, IV

[11] Patent Number: 4,797,256
[45] Date of Patent: Jan. 10, 1989

[54] REGISTRATION DEVICE FOR BLOOD TEST STRIPS

[75] Inventor: Thomas M. Watlington, IV, Indianapolis, Ind.

[73] Assignee: Boehringer Mannheim Corporation, Indianapolis, Ind.

[21] Appl. No.: 59,789

[22] Filed: Jun. 5, 1987

[51] Int. Cl.$^4$ .................... G01N 1/48; G01N 21/06; B01L 9/00

[52] U.S. Cl. ........................ 422/58; 422/56; 422/104

[58] Field of Search ................... 422/56–58, 422/104

[56] References Cited

U.S. PATENT DOCUMENTS 4,128,400 12/1976 Mühlböck et al. .................. 422/104
4,336,337 6/1980 Wallis et al. ........................ 422/58
4,518,565 6/1983 Boger et al. ....................... 422/104

Primary Examiner—Sidney Marantz
Assistant Examiner—Lyle Alfandary-Alexander
Attorney, Agent, or Firm—Perman & Green

[57] ABSTRACT

A ring-shaped registration device for receiving and holding an activated test strip having a reagent area adapted to receive a blood sample. The registration device is slidably received on the outer peripheral surface of a cylindrical vial on which markings to indicate a range of possible results which might be evidenced by a blood sample. The device includes a central member having a support region for slidably receiving the activated test strip and defining a window for outlining markings on the surface of the vial and on the reagent area of the activated test strip. The reagent area is held in substantially tangential relationship relative to the outer peripheral surface of the vial so as to be selectively positioned intermediate adjacent markings on the surface of the vial. This enables the user to compare an actual blood sample with the range of possible conditions and match the sample with the markings on the vial.

19 Claims, 3 Drawing Sheets

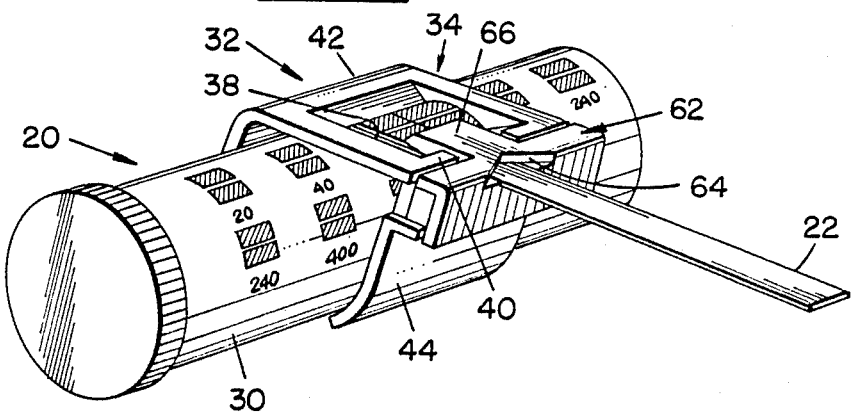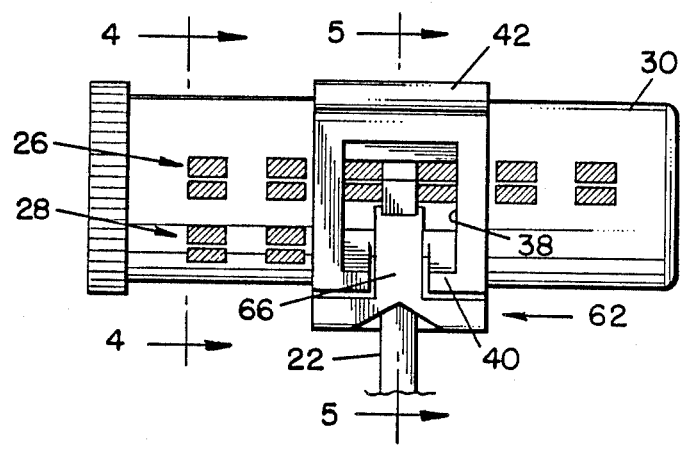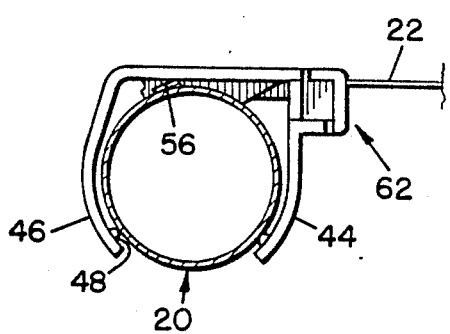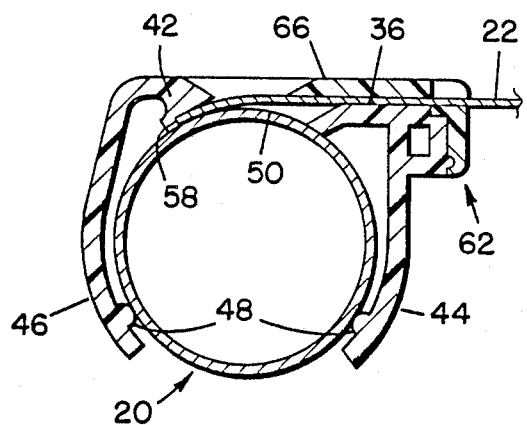

REGISTRATION DEVICE FOR BLOOD TEST STRIPS

BACKGROUND OF THE INVENTION

I. Field of the Invention

The present invention relates generally to a system of testing for glucose in whole blood and, more particularly, to a registration device for improving the ability of a user to obtain an accurate indication of the glucose level in his blood.

II. Description of the Prior Art

The present invention is intended for use with known self-administered tests used for determining the level of glucose in whole blood. Such a test has been developed and is marketed by Boehringer Mannheim Corporation of Indianapolis, Indiana under the registered trademark "CHEMSTRIP bG". In a customary manner, a cylindrical capped container or vial is provided with markings graduated by color as on a paper label adhesively applied to its outer peripheral surface. The markings are indicative of a range of possible conditions which might be evidenced by a blood sample. The vial contains a quantity of elongated flexible strips, each of which is intended for an individual test. Each strip is provided with a reagent area adjacent one end thereof. The normally inactive reagent area is activated when the user places a large drop of whole blood thereon. According to the usual test, the user simultaneously starts a timer. After a specified time interval, for example, 60 seconds, the blood is wiped off the reagent area as by the use of a dry cotton ball. After an additional specified time interval, for example, again 60 seconds, the color or colors appearing in the reagent area are matched by the user with the graduated markings on the outer surface of the vial. At this point, if a match is substantially obtained, the glucose level can be determined. However, if the color developed is darker than that of the darkest color appearing on the vial for the two minutes (120 second) range, then it is necessary to wait an additional 60 seconds before comparing the final reaction color with the color scale relating to a three minute duration.

Time is an important factor in performing the test. That is, the reagent area of the test strip continues to darken with the passage of time. Therefore, the test is only accurate if a color match is obtained at a finite point in time, that is, precisely after two minutes for the two minute scale or, precisely after three minutes for the three minute scale.

However, it will be appreciated that the users of self-administered tests such as the CHEMSTRIP bG test are diabetics who, in some instances, are unsteady with their hands. As a result, it may be difficult for such a user to obtain a color match within the necessarily tightly controlled duration of time.

It was with the knowledge of this drawback of the prior art that the present invention has been conceived and now reduced to practice.

SUMMARY OF THE INVENTION

The present invention is directed toward a ring-like registration device for receiving and holding an activated test strip having a reagent area adapted to receive a blood sample. The device is slidably received on the outer peripheral surface of a cylindrical vial on which are provided markings indicative of a range of possible results which might be evidenced by the blood sample.

The device includes a central member having a support region for slidably receiving the activated test strip and defining a window for outlining markings on the surface of the vial and on the reagent area of the activated test strip. The reagent area is held in substantially tangential relationship relative to the outer peripheral surface of the vial so as to be selectively positioned intermediate adjacent markings on the surface of the vial. This enables the user to compare an actual blood sample with the range of possible conditions and match the sample with the markings on the vial.

The invention exhibits a number of features and benefits. In a first instance of such, it is of a simple construction which can be easily and inexpensively manufactured. Indeed, it might be desirable to provide the device of the invention with each vial and to discard it with the vial when the contained supply of test strips is exhausted.

As a further benefit, the invention can be readily used with the existing CHEMSTRIP bG glucose test system without requiring modification of that system in any manner.

Additionally, the operation of the invention can be readily learned and can be easily used by persons experiencing unsteadiness of hand. Furthermore, it assures accurate analysis even when performed by such an unsteady user.

Another feature of the invention resides its ability to be easily disassembled for cleaning, then re-assembled for use once again.

Other and further features, objects, advantages, and benefits of the invention will become apparent from the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention and, together with the description, serve to explain the principles of the invention in general terms. Like numerals refer to like parts through the disclosure.

BRIEF DESCRIPTION OF THE DRAWINGS

FIG. 2 is a perspective view of a registration device embodying the invention and illustrating its use in actual practice;

FIG. 3 is a top plan view of the structure illustrated in FIG. 2;

FIGS. 4 and 5 are cross section views taken, respectively, along lines 4—4 and 5—5 in FIG. 3;

DETAILED DESCRIPTION OF THE PREFERRED EMBODIMENTS

Figure 1:
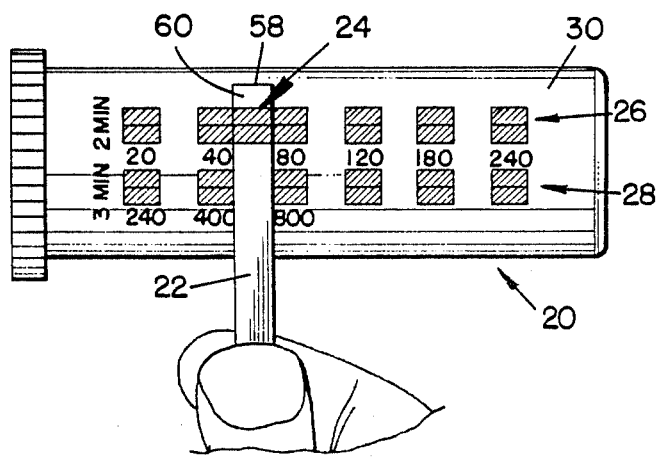
FIG. 1 is a side elevation view generally illustrating one step of a known procedure for determining the level of glucose in a blood sample.

Turn now to the drawings and initially to FIG. 1 which illustrates a cylindrical capped container or vial 20 which may utilized for purposes of a self-administered test for determining the level of glucose in whole blood. The test may be, for example, one marketed by Boehringer Mannheim Corporation under the registered trademark CHEMSTRIP bG.

According to a known procedure, an elongated test strip 22 of flexible material is removed from the vial 20 which may contain a large quantity of similar test strips. The test strip has a reagent area 24 adapted to receive a large drop of whole blood in a known manner. The vial 20 is provided with a plurality of markings thereon graduated by color as on a paper label which may be adhesively applied to an outer peripheral surface 30 of the vial. A first aligned series 26 of graduated markings reflect a range of possible results of a two minute test while a second aligned series 28 of graduated markings reflect a range of possible results of a three minute test. The meaning of a two minute test and of a three minute test will now be explained.

At the moment that the user places a large drop of blood on the reagent area 24 of the test strip 22, he simultaneously starts a timer in operation. According to the test, after exactly 60 seconds have passed, he is required to wipe off the blood with a dry cotton ball or in some other suitable fashion. After an additional 60 seconds has passed, the reagent area 24 is then placed proximate to the graduated markings 26 and, specifically, between that pair of markings whose color or colors most closely matches the color or colors of the reagent area 24 of the test strip 22. If a match, or near match, is achieved, the glucose level registered in units of mg/dL is thereby determined. However, in the event the color developed at the reagent area 24 is darker than the color or colors portrayed by the graduated markings 26 for a level of 240 mg/dL (that is, the darkest color portrayed by any of the markings within the first set 26), the user is required to wait an additional 60 seconds after which the reaction color of the reagent area 24 is compared or matched with the second series of graduated markings 28. It will be appreciated that intermediate values of glucose concentrations can be estimated when the colors of the reagent area 24 are intermediate those on the vial 20.

The test just described is accurate and highly desirable. However, it has previously been mentioned, that it sometimes occurs that a diabetic person who would be the user of such a test would be sufficiently unsteady of hand that an accurate match could not be achieved within the restricted time period available.

The invention has been conceived and developed in order to assure an accurate result even when the user is unsteady of hand. Turn now to FIGS. 2 through 5 which illustrate the use of a registration device 32, which embodies the invention, in combination with the vial 20 which is of known shape, size, and construction.

As illustrated, the registration device 32 is slidably received on the outer peripheral surface 30 of the vial 20. It includes a central member 34 having a support region 36 (see especially FIG. 6) for slidably receiving the activated test strip 22, that is a test strip on which the blood sample (a drop) has been applied to the reagent area 24. The central member 34 also defines a window 38 extending therethrough for outlining or placing in registration, simultaneously, at least one set of the graduated markings 26, 28 on the peripheral surface 30 and on the reagent area 24 of the activated test strip 22 (see especially FIGS. 2 and 3).

The central member 34 includes first and second opposed side members 40 and 42, respectively, and the registration device 32 includes a pair of legs 44, 46 which extend away from the first and second side members 40, 42, respectively. Elongated protuberances formed on the inside of the side member 40, 42 serve as gripping members 48 at locations distant from the side members 40, 42 and serve to slidably engage the outer peripheral surface 30 of the vial 20. The central member 34 also includes an arcuate undersurface 50 which generally encompasses the window 38 and conforms to the outer peripheral surface 30 for slidable engagement therewith. Thus, it will be appreciated that the registration device 32 is slidably movable on the gripping members 48 and on the arcuate undersurface 50 both longitudinally along the length of the vial and circumferentially thereof. Of course, as the registration device 32 is moved, the window 38 is likewise moved.

Figure 14:
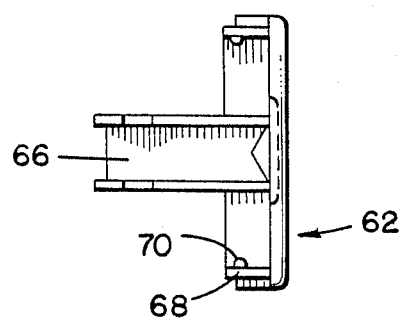
FIGS. 11, 12, 13, and 14, are, respectively, side elevation, top plan, front elevation, and bottom plan views of a subcomponent of the invention.
Figure 6:
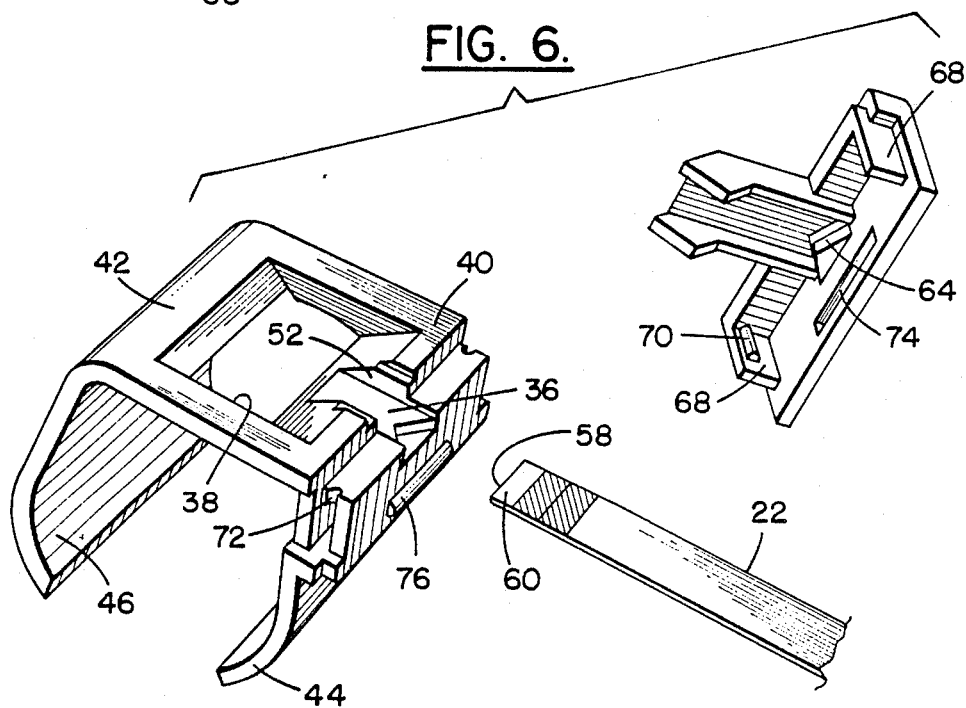
FIG. 6 is a perspective exploded view of the invention and of a test strip utilized therewith.
Figure 7:
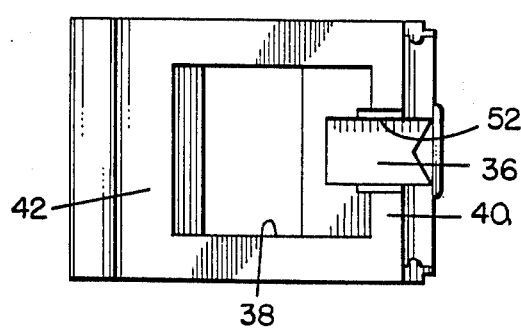
FIGS. 7, 8, and 9 are top plan, front, and side elevation views, respectively, of a main component of the invention.
Figure 8:
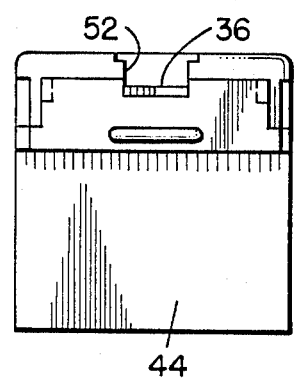
Figure 9:
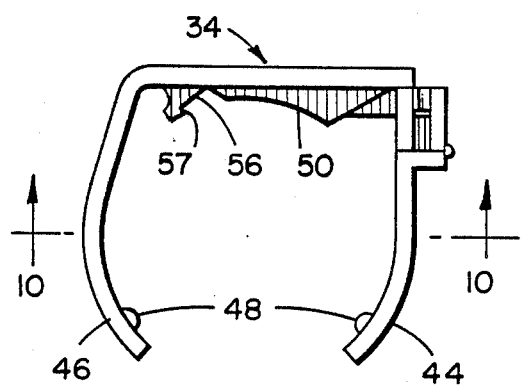
Figure 11:
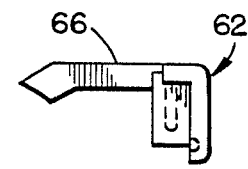
Figure 12:
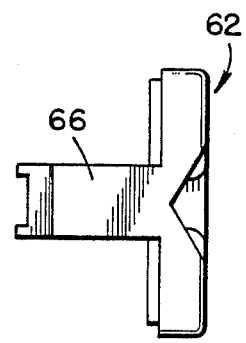
Figure 10:
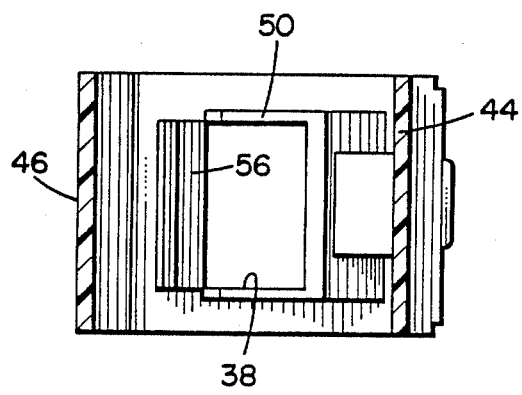
FIG. 10 is a cross section view taken generally along line 10—10 in FIG. 9.
Figure 13:
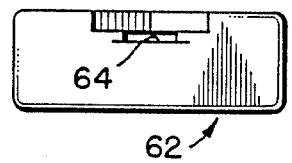

Viewing especially FIGS. 6–8, the side member 40 defines an entry aperture 52 for slidably receiving a test strip 22 therethrough. The entry aperture 52 and the support region 36 coact to guide the test strip into registration within the window 38.

The side member 42 is formed with a slot 56 adjacent the window 38 which extends to a terminal surface 57 for engageably receiving an extreme end 58 of the test strip 22. As seen particularly in FIGS. 1 and 6, the reagent area 24 is spaced from the extreme end 58 by a region 60 which assures that the reagent area 24 is properly aligned with the markings 26 or 28 when those markings are within the opening defined by the window 38. With region 60 positioned proximate to the slot 56 and the extreme end 58 engaged with the terminal surface 57, the test strip 22 assumes an orientation which is substantially tangential relative to the outer peripheral surface 30 of the vial 20.

An added feature of the invention resides in the provision of a subcomponent 62 (FIGS. 11-14) which is removably mounted on a main component which includes the central member 34 and outwardly extending legs 44, 46. The subcomponent 62 defines an opening 64 for slidably receiving the test strip 22 and includes a nose member 66 which extends beyond the opening 64 and overlies the support region 36 when the subcomponent 62 is mounted on the side member 40. The subcomponent 62 includes opposed side walls 68, each of which has an elongated key 70 engageable with mating slots 72 formed in the side member 40. This construction enables the subcomponent to be moved between a fully disengaged position and an engaged position abutting the side member 40. Furthermore, the subcomponent 62 is preferably formed of at least moderately resilient material and includes an elongated slot 74 which cooperatively receives for engagement therein a mutually sized and shaped detent member 76 formed in the side member 40. The detent member 76 and slot 74 are mutually engaged when the subcomponent 62 reaches its operational position on the side member 40, that is, the position it assumes when it is ready to admit a test strip 22 within the opening 64 for advancement to the window 38.

When the opening 64, the entry aperture 52, and the support region 36 become undesirably filled or clogged with dried blood or other undesired residue, the subcomponent 62 can be pushed upwardly (see especially FIGS. 2, 4, and 5) so that the slot 74 is released from the detent member 76, allowing the subcomponent to move in the direction afforded by the keys 70 and mating slots 72 until the subcomponent 62 is completely free of the remainder of the structure. When this occurs, the subcomponent 62 can be cleaned as well as the remainder of the registration device 32. Thereupon, the subcomponent 62 can be reattached.

While a preferred embodiment of the invention has been disclosed in detail, it should be understood by those skilled in the art that other various modifications may be made to the illustrated embodiment without departing from the scope of the invention as described in the specification and defined in the appended claims.

What is claimed is:

1. A system of testing for glucose in whole blood comprising:
   a cylindrical vial for containing a plurality of inactivated test strips which are selectively removable therefrom, each test strip provided with a reagent area adapted to receive a blood sample thereon and thereby being activated to indicate a particular color consistent with the condition of the blood and the time elapsed since reception of the blood sample thereon, said vial having an outer peripheral surface;
   a plurality of graduated markings on said peripheral surface providing a range of different colors which are indicative of a range of possible conditions which might be evidenced by an activated test strip;
   holder means slidably mounted on said outer peripheral surface and including a support region for slidably receiving the reagent area of an activated test strip, said holder means defining a window for outlining, simultaneously, at least one of said markings on said peripheral surface and on the reagent area of the activated test strip;
   thereby enabling the reagent area on the activated test strip to be matched with an appropriate one of said markings on said peripheral surface to thereby indicate the condition of the blood being sampled.

2. A system as set forth in claim 1 wherein said holder means includes;
   a main component including said support region and defining the window; and
   a subcomponent removably mounted on said main component adjacent said support region, said subcomponent defining an opening for slidably receiving a test strip therethrough and including guide means cooperatively positioned relative to the opening for guiding the test strip into the window when said subcomponent is mounted on said main component.

3. A system as set forth in claim 2 wherein said subcomponent is movable between a disengaged position separate from said main component and an engaged position intimately abutting said main component, and including:
   mutually cooperating key means on said main component and on said subcomponent for cooperatively guiding said subcomponent to said engaged position; and
   mutually engaging detent means on said main component and on said subcomponent, respectively, for releasably holding said subcomponent in said engaged position.

4. A system as set forth in claim 1 wherein said holder means includes:
   first and second opposed side members; and including:
   first and second opposed legs integral with and extending away from said first and second side members, respectively, said first leg having a gripping member distant from said first side member for slidably engaging said outer peripheral surface and said second leg having a gripping member distant from said second side member for slidably engaging said outer peripheral surface;
   whereby the window can be moved both longitudinally along the length of said vial and circumferentially thereof.

5. A system as set forth in claim 4 wherein said first and second legs are resilient relative to said first and second side members, respectively, and are biased towards each other so as to securely engage said outer peripheral surface.

6. A system as set forth in claim 4 wherein said central member includes:
   an arcuate undersurface generally encompassing the window therein for slidably engaging the outer peripheral surface of said vial.

7. A system as set forth in claim 4 wherein said first side member defines an entry aperture for slidably receiving a test strip therethrough and includes:
   guide means cooperatively positioned relative to the entry aperture for guiding the test strip into the window.

8. A system as set forth in claim 7 wherein said second side member includes a slot adjacent the window for receiving an end of the test strip proximate to the reagent area thereof for thereby stabilizing the test strip as said holder means is moved on said peripheral surface.

9. A system as set forth in claim 7 wherein said plurality of markings include:
   individual markings at a plurality of spaced locations along the length of said vial, adjacent ones of said markings being spaced by a distance substantially equal to the width of the test strip enabling movement of said holder means on said outer peripheral surface such that the reagent area of an activated test strip is positioned intermediate said adjacent markings.

10. Apparatus enabling the reagent area of an activated test strip to which a blood sample has been applied to be matched with graduated markings indicative of a range of possible conditions which might be evidenced by a blood sample, which markings are provided on the outer peripheral surface of a cylindrical vial, comprising:
    holder means slidably mounted on the outer peripheral surface of the vial and including a central member having a support region for slidably receiving and holding the activated test strip substantially tangent to the outer peripheral surface of the vial, said central member defining a window for outlining, simultaneously, at least one of the markings on the peripheral surface and on the reagent area of the activated test strip.

11. Apparatus as set forth in claim 10 wherein said central member includes:

an arcuate undersurface generally encompassing the window therein for slidably engaging the outer peripheral surface of the vial.

12. Apparatus as set forth in claim 10 wherein the plurality of markings on the outer peripheral surface of the vial include individual markings at a plurality of spaced locations along the length of the vial, adjacent ones of the markings being spaced by a distance generally equal to the width of the test strip; and wherein said central member includes:

first and second opposed side members; and including:

first and second opposed legs integral with and extending away from said first and second side members, respectively, having a gripping member distant from said first side member for slidably engaging the outer peripheral surface of the vial and said second leg having a gripping member distant from said second side member for slidably engaging the outer peripheral surface of the vial;

said first side member defining an entry aperture for slidably receiving a test strip therethrough and including guide means cooperatively positioned relative to the entry aperture for guiding the test strip into the window;

said second side member including a slot adjacent the window for receiving an end of the test strip proximate to the reagent area thereof for thereby stabilizing the test strip and holding the test strip in a substantially tangential relationship relative to the outer peripheral surface of the vial such that the reagent area of an activated test strip can be selectively positioned intermediate adjacent markings on the outer peripheral surface of the vial.

13. Apparatus as set forth in claim 12 wherein said central member includes:

an arcuate undersurface generally encompassing the window therein for slidably engaging the outer peripheral surface of the vial.

14. A system as set forth in claim 10 wherein said holder means includes:

a main component including said support region and defining the window; and a subcomponent removably mounted on said main component adjacent said support region, said subcomponent defining an entry aperture for slidably receiving a test strip therethrough and including guide means cooperatively positioned relative to the entry aperture for guiding the test strip into the window when said subcomponent is mounted on said main component.

15. A system as set forth in claim 14 wherein said subcomponent is movable between a disengaged position separate from said main component and an engaged position intimately abutting said main component; and including:

mutually cooperating key means on said main component and on said subcomponent for cooperatively guiding said subcomponent to said engaged position; and mutually engaging detent means on said main component and on said subcomponent, respectively, for releasably holding said subcomponent in said engaged position.

16. Apparatus as set forth in claim 10 wherein said central member includes:

first and second opposed side members; and including:

first and second opposed legs integral with and extending away from said first and second side members, respectively, said first leg having a gripping member distant from said first side member for slidably engaging the outer peripheral surface of the vial and said second leg having a gripping member distant from said side member for slidably engaging the outer peripheral surface of the vial;

whereby the window can be moved both longitudinally along the length of the vial and circumferentially thereof.

17. Apparatus as set forth in claim 16 wherein said first and second legs are resilient relative to said first and second side members, respectively, and are biased towards each other so as to securely engage said outer peripheral surface.

18. Apparatus as set forth in claim 16 wherein said first side member defines an entry aperture for slidably receiving a test strip therethrough and includes:

guide means cooperatively positioned relative to the entry aperture for guiding the test strip into the window.

19. Apparatus as set forth in claim 18 wherein said second side member includes:

a slot adjacent the window for receiving an end of the test strip proximate to the reagent area thereof for thereby stabilizing the test strip as said holder means is moved on the peripheral surface of the vial

* * * * *